US012667370B2

(12) United States Patent
Zhang et al.

(10) Patent No.: US 12,667,370 B2
(45) Date of Patent: Jun. 30, 2026

(54) MODULAR MULTIFUNCTIONAL PELVIC FIXATION HEMOSTATIC DEVICE

(71) Applicant: Air Force Medical University of Chinese People's Liberation Army, Xi'an (CN)

(72) Inventors: Keying Zhang, Xi'an (CN); Wei Hu, Xi'an (CN); Weijun Qin, Xi'an (CN); Donghui Han, Xi'an (CN); Yuankang Zou, Xi'an (CN); Chao Zhang, Xi'an (CN); Xiangliang Meng, Xi'an (CN); Sikai Li, Xi'an (CN); Lingdi Chang, Xi'an (CN); Bo Yang, Xi'an (CN)

(73) Assignee: AIR FORCE MEDICAL UNIVERSITY OF CHINESE PEOPLE'S LIBERATION ARMY, Xi'an (CN)

( * ) Notice: Subject to any disclaimer, the term of this patent is extended or adjusted under 35 U.S.C. 154(b) by 99 days.

(21) Appl. No.: 18/824,856

(22) Filed: Sep. 4, 2024

(65) Prior Publication Data

US 2024/0423640 A1      Dec. 26, 2024

Related U.S. Application Data

(63) Continuation of application No. PCT/CN2023/140825, filed on Dec. 22, 2023.

(30) Foreign Application Priority Data

Dec. 31, 2022     (CN) .......................... 202211739021.6

(51) Int. Cl.
*A61B 17/135*          (2006.01)

(52) U.S. Cl.
CPC ................................ *A61B 17/1355* (2013.01)

(58) Field of Classification Search
CPC ... A61B 17/12; A61B 17/1325; A61B 17/135; A61B 17/1355; A61H 39/04
See application file for complete search history.

(56) References Cited

U.S. PATENT DOCUMENTS

2020/0060878 A1 *    2/2020    Oh ...................... A61F 13/0213

FOREIGN PATENT DOCUMENTS

CN            101485599 A  *  7/2009
CN            209899725 U  *  1/2020

* cited by examiner

*Primary Examiner* — Mohamed G Gabr
*Assistant Examiner* — Khoa Tan Le

(57) ABSTRACT

A modular multifunctional pelvic fixation hemostatic device is provided, the device includes a fixing strap, a lock catch, an auxiliary fixing assembly, a hemostatic assembly, a press inflator, a perineal pocket, a hemostatic excipient pad and an auxiliary compressing assembly, a patient pelvic position is fixed through the fixing strap and the lock catch, and stability of the fixing strap in the pelvic position is improved through the auxiliary fixing assembly, thus avoiding a movement of the fixing strap during patient transporting and dragging. Great vessels in a junctional area are effectively compressed through the hemostatic assembly, thus ensuring a compression hemostasis effect of the great vessels. The hemostatic excipient pad is in full contact with a wound of the patient through the auxiliary compressing assembly, thus covering and dressing bone protrusions and bone depressions of the patient, and achieving integrated pelvic fixation, wound hemostasis, and dressing.

7 Claims, 5 Drawing Sheets

MODULAR MULTIFUNCTIONAL PELVIC FIXATION HEMOSTATIC DEVICE

TECHNICAL FIELD

The disclosure relates to the field of pelvic fixation hemostasis technologies, and more particularly to a modular multifunctional pelvic fixation hemostatic device.

BACKGROUND

A retrospective analysis of 4596 US military war wound deaths from October 2001 to June 2011 found that 90.9% of war wound deaths are related to hemorrhage. Among the fatal hemorrhage death cases, 67.3% are somatic detachment hemorrhage which is incompressible and difficult to treat, followed by treatable junctional hemorrhage (19.2%) and limb hemorrhage (13.5%). Since 2005, with increasing use of limb tourniquets by the US military, a war wound mortality rate caused by limb hemorrhage has significantly decreased, according to statistics, as of 2011, the mortality rate caused by limb hemorrhage dropped to 2.6% of total deaths, and a decrease of 67%. In view of a great success of the limb tourniquets in controlling hemorrhage and improving survival rate, people's attention has shifted from hemorrhage control in other parts to hemorrhage control in a junctional area. According to a review of American Tactical War Injury Treatment Committee in 2013, nearly one-fifth of fatal hemorrhage occurred in the junctional area (such as a groin junctional area), and incidence of death caused by hemorrhage at the junctional area has exceeded that of hemorrhage in limbs. Regrettably, China lags behind European and American military powers in research and development of hemostatic devices in the junctional areas, and corresponding ability to treat war wounds need to be improved urgently.

In view of the fact that bleeding of great vessels (e.g., femoral artery or femoral vein) in the groin junctional area is often complicated with pelvic fracture, neurovascular injury of fracture fragments, bleeding of perineum and buttocks, etc., a modular multifunctional pelvic fixation hemostatic device is innovatively designed to simultaneously achieve functions of pelvic binding and fixation, compression hemostasis of the great vessels in the junctional area, pressure dressing of bleeding wounds in the perineum and the buttocks, which provides a powerful tool for the treatment of war wounds in the junctional area.

SUMMARY

A purpose of the disclosure is to provide a modular multifunctional pelvic fixation hemostatic device, to solve problems proposed in the above background.

In order to achieve the above purpose, the disclosure provides the following technical solutions:

A modular multifunctional pelvic fixation hemostatic device is provided, and the device includes a fixing strap, a lock catch, an auxiliary fixing assembly, a hemostatic assembly, press inflators, a perineal pocket, a hemostatic excipient pad and an auxiliary compressing assembly.

The fixing strap is configured to wrap around a pelvic position of a patient; two ends of the lock catch are respectively disposed on two ends of the fixing strap, and the lock catch is configured to fix a length of the fixing strap wrapped around an outside of the pelvic position of the patient; the auxiliary fixing assembly is disposed on two sides of the fixing strap, and the auxiliary fixing assembly is configured to fix the fixing strap on the pelvic position of the patient.

The hemostatic assembly is disposed on the fixing strap, and is configured to compress great vessels in a junctional area; and the press inflators are connected to the hemostatic assembly, and are configured to adjust a volume of the hemostatic assembly.

The perineal pocket is disposed on a middle of the fixing strap, and is configured to cover and dress a perineum and buttocks of the patient; the hemostatic excipient pad is disposed on a surface of the perineal pocket; and the auxiliary compressing assembly is disposed on an inside of the perineal pocket, and is configured to perform pressure hemostasis on a bone protrusion area and a depression area of the perineum and the buttocks of the patient.

In an embodiment, the auxiliary fixing assembly includes limiting straps, connection strips, racks, positioning brackets, limiting brackets, positioning racks, positioning rods and first elastic elements; the limiting straps are disposed on the two sides of the fixing strap, respectively; the connection strips are disposed on two ends of each of the limiting straps proximate to the lock catch, respectively; the racks are disposed on surfaces of the connection strips, respectively; the positioning brackets are fixedly installed on ends of the fixing strap proximate to the lock catch, respectively; the limiting brackets are disposed in the positioning brackets and are disposed proximate to the racks, respectively; the positioning racks are disposed in the limiting brackets, respectively; the positioning rods are fixedly installed on the positioning racks, respectively, and each of the positioning rods penetrates through an end of the positioning bracket; and the first elastic elements are respectively sleeved on outsides of the positioning rods, and each of the first elastic element is configured to adjust a position of the positioning rack inside the limiting bracket, to make the positioning rack be connected to the rack.

In an embodiment, the hemostatic assembly includes first hemostatic air bags, first valves, first VELCRO-type fastening elements, second hemostatic air bags, second valves and second VELCRO-type fastening elements.

The first hemostatic air bags are disposed on ends of an inside of the fixing strap proximate to the lock catch, respectively; a section shape of each of the first hemostatic air bag is arc-shaped, and each of the first hemostatic air bags defines a first air intake; the first valves are installed on the first air intakes of the first hemostatic air bags, respectively; the first VELCRO-type fastening elements are respectively installed on the first hemostatic air bags, and each of the first VELCRO-type fastening element is configured to connect the first hemostatic air bag and the fixing strap.

The second hemostatic air bags are disposed on an outside of the fixing strap; a section shape of each of the second hemostatic air bags is elliptical, and each of the second hemostatic air bag defines a second air intake; the second valves are installed on the second air intakes of the second hemostatic air bags, respectively; and the second VELCRO-type fastening elements are respectively installed on surfaces of the second hemostatic air bags, and each of the second VELCRO-type fastening elements is configured to connect the second hemostatic air bag and the fixing strap.

In an embodiment, the auxiliary compressing assembly includes: a positioning plate, a resilient, a positioning ring, a water bag, sealing plugs and an adjusting assembly.

The positioning plate is disposed inside the perineal pocket; the resilient pad is disposed on the positioning plate, and the resilient pad is filled with foaming agent powder therein; the positioning ring is disposed on a middle of the positioning plate; the water bag is disposed on the positioning ring, and the positioning ring is in communication with an inside of the water bag; and the positioning ring defines drain holes.

The sealing plugs are disposed in the drain holes, respectively; the adjusting assembly is disposed inside the positioning ring, and is connected to the sealing plugs, and the adjusting assembly is configured to adjust positions of the sealing plugs on the drain holes, to thereby open and seal the drain holes.

In an embodiment, the adjusting assembly includes: moving rods, limiting assemblies, a drive rod, a drive rack and connection assemblies.

The moving rods are fixedly connected to the sealing plugs, respectively, and the moving rods are disposed inside the positioning ring; the limiting assemblies are disposed between a corresponding one of the moving rods and the positioning plate, and each of the limiting assemblies is configured to limit a moving track of the moving rod, and adjust a position of the moving rod.

The drive rod is disposed on the middle of the positioning plate, and is fixedly connected to the middle of the positioning plate; the drive rack is fixedly installed on an end of the drive rod located inside the positioning ring; and each of the connection assemblies is disposed between the drive rack and a corresponding one of the moving rods, and each of the connection assemblies is configured to move the position of the moving rod when the drive rod and the drive rack rotate, to thereby make the scaling plug away from the drain hole.

In an embodiment, each of the limiting assemblies includes a slide rail, a moving block and a second elastic element.

The slide rail is fixedly disposed on the positioning plate, and is located inside the positioning ring; the moving block is disposed inside the slide rail and fixedly connected to an outer wall of the moving rod, the moving block is slidably connected to the slide rail, and the slide rail is configured to keep the moving rod moving along inside the slide rail; and the second elastic element is disposed between the moving block and the slide rail.

In an embodiment, each of the connection assemblies includes a fixing rod, a connection rack, a first rotating bracket, a connection rod and a second rotating bracket.

The fixing rod is disposed on the positioning plate, and is located on a side of the drive rod; the connection rack is installed on an outside of the fixing rod and is rotatably connected to the fixing rod; the first rotating bracket is disposed on a surface of the connection rack; the connection rod is disposed on an outside of the first rotating bracket; the second rotating bracket is disposed on an end of the connection rod facing away from the first rotating bracket, and the second rotating bracket is fixedly connected to the corresponding moving rod; and the drive rack is meshed with the connection rack.

Compared to the related art, beneficial effects of the disclosure are as follows.

In the modular multifunctional pelvic fixation hemostatic device provided by the disclosure, the pelvic position of the patient can be fixed through the fixing strap and the lock catch, stability of the fixing strap on the pelvic position of the patient is improved through the auxiliary fixing assembly, thus avoiding a movement of the fixing strap during patient transporting, dragging, and other processes; the great vessels in the junctional area are effectively compressed through the hemostatic assembly on the fixing strap, thus ensuring a compression hemostasis effect of the great vessels; the hemostatic excipient pad is in full contact with wounds of the perineum and the buttocks of the patient through the auxiliary compressing assembly, thus covering and dressing the bone protrusion area and the depression area of the patient, an operation of the hemostatic device is convenient, so as to achieve integrated pelvic fixation, wound hemostasis, and dressing.

LIST OF REFERENCE NUMBERS

Figure 1:
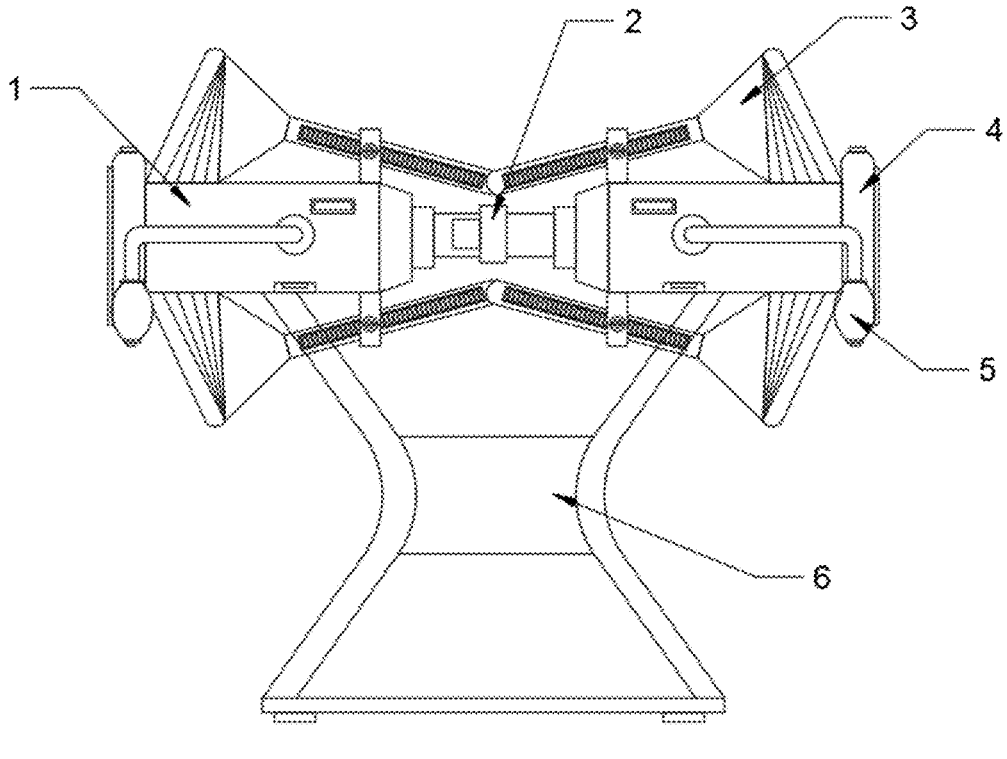
FIG. 1 illustrates a schematic structural diagram of a modular multifunctional pelvic fixation hemostatic device according to an embodiment of the disclosure.

1-fixing strap; 2-lock catch; 3-auxiliary fixing assembly; 31-limiting strap; 32-connection strip; 33-rack; 34-positioning bracket; 35-limiting bracket; 36-positioning rack; 37-positioning rod; 38-first elastic element; 4-hemostatic assembly; 41-first hemostatic air bag; 42-first air intake; 42-first valve; 44-second hemostatic air bag; 45-first VELCRO-type fastening element; 46-second air intake; 47-second valve; 48-second VELCRO-type fastening element; 5-press inflator; 6-perineal pocket; 7-hemostatic excipient pad; 8-auxiliary compressing assembly; 81-positioning plate; 82-resilient pad; 83-foaming agent powder; 84-positioning ring; 85-water bag; 86-drain hole; 87-sealing plug; 88-adjusting assembly; 881-moving rod; 882-limiting assembly; 8821-slide rail; 8822-moving block; 8823-second clastic element; 883-drive rod; 884-drive rack; 885-connection assembly; 8851-fixing rod; 8852-connection rack; 8853-first rotating bracket; 8854-connection rod; 8855-second rotating bracket.

DETAILED DESCRIPTION OF EMBODIMENTS

In order to make purposes, technical solutions and advantages of the disclosure more clearly and understandably, the disclosure will be further described in detail in conjunction with drawings and embodiments below. It should be understood that the embodiments described here are merely used to describe the disclosure, and are not used to limit the disclosure.

A specific implementation of the disclosure is described in detail in conjunction with the embodiments below.

Embodiment 1

As shown in FIGS. 1-8, a modular multifunctional pelvic fixation hemostatic device is provided in the embodiment of the disclosure, and the hemostatic device includes a fixing strap 1, a lock catch 2, an auxiliary fixing assembly 3, a hemostatic assembly 4, press inflators 5, a perineal pocket 6, a hemostatic excipient pad 7, and an auxiliary compressing assembly 8.

The fixing strap 1 is configured to wrap around a pelvic position of a patient. Two ends of the lock catch 2 are respectively disposed on two ends of the fixing strap 1, and the lock catch 2 is configured to fix a length of the fixing strap 1 wrapped around the pelvic position of the patient. Two sides of the fixing strap 1 are provided with the auxiliary fixing assembly 3, and the auxiliary fixing assembly 3 is configured to fix the fixing strap 1 in the pelvic position of the patient.

The hemostatic assembly 4 is disposed on the fixing strap 1, and is configured to compress great vessels in a junctional area. The hemostatic assembly 4 is connected to the press inflators 5, and the press inflators 5 are configured to adjust a volume of the hemostatic assembly 4.

The perineal pocket 6 is disposed on a middle of the fixing strap 1, and is configured to cover and dress a perineum and buttocks of the patient. A surface of the perineal pocket 6 is provided with the hemostatic excipient pad 7, and an inside of the perineal pocket 6 is provided with the auxiliary compressing assembly 8, and the auxiliary compressing assembly 8 is configured to perform pressure hemostasis on a bone protrusion area and a depression area of the perineal and the buttocks of the patient.

In the embodiment, the pelvic position of the patient can be fixed through the fixing strap 1 and the lock catch 2, stability of the fixing strap 1 in the pelvic position of the patient is improved through the auxiliary fixing assembly 3, thus avoiding a movement of the fixing strap 1 during patient transporting, dragging, and other processes; the great vessels in the junctional area are effectively compressed through the hemostatic assembly 4 on the fixing strap 1, thus ensuring a compression hemostasis effect of the great vessels; the hemostatic excipient pad 7 is in full contact with wounds of the perineum and the buttocks of the patient through the auxiliary compressing assembly 8, thus covering and dressing the bone protrusion area and the depression area of the patient, an operation of the hemostatic device is convenient, so as to achieve integrated pelvic fixation, wound hemostasis, and dressing. The perineal pocket 6 is a triangular structure or a straight angle structure. When the perineal pocket 6 is the straight angle structure, a clip-style tourniquet is installed on an end of a part of the perineal pocket 6 proximate to a thigh of the patient, which can block active bleeding of lower limb wound caused by arterial blood supply from top to bottom, and has a certain hemostatic effect on inguinal wound bleeding caused by venous reflux from bottom to up.

Figure 2:
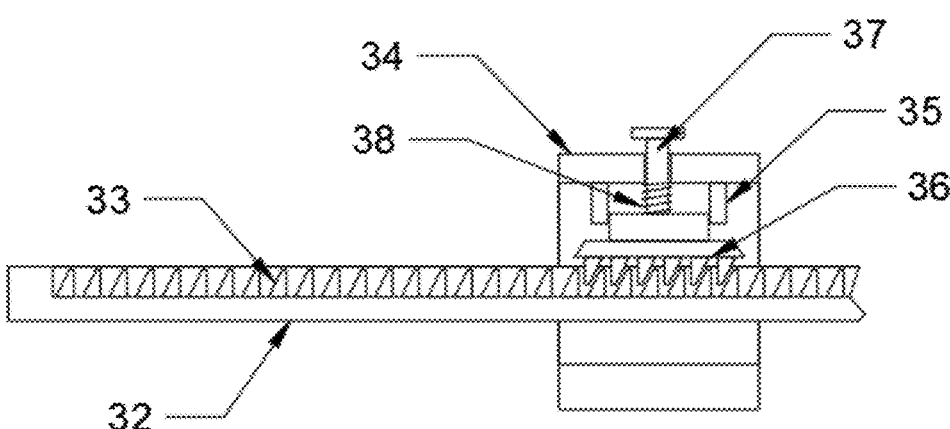
FIG. 2 illustrates a schematic structural diagram of an auxiliary fixing assembly of the modular multifunctional pelvic fixation hemostatic device according to an embodiment of the disclosure.
Figure 5:
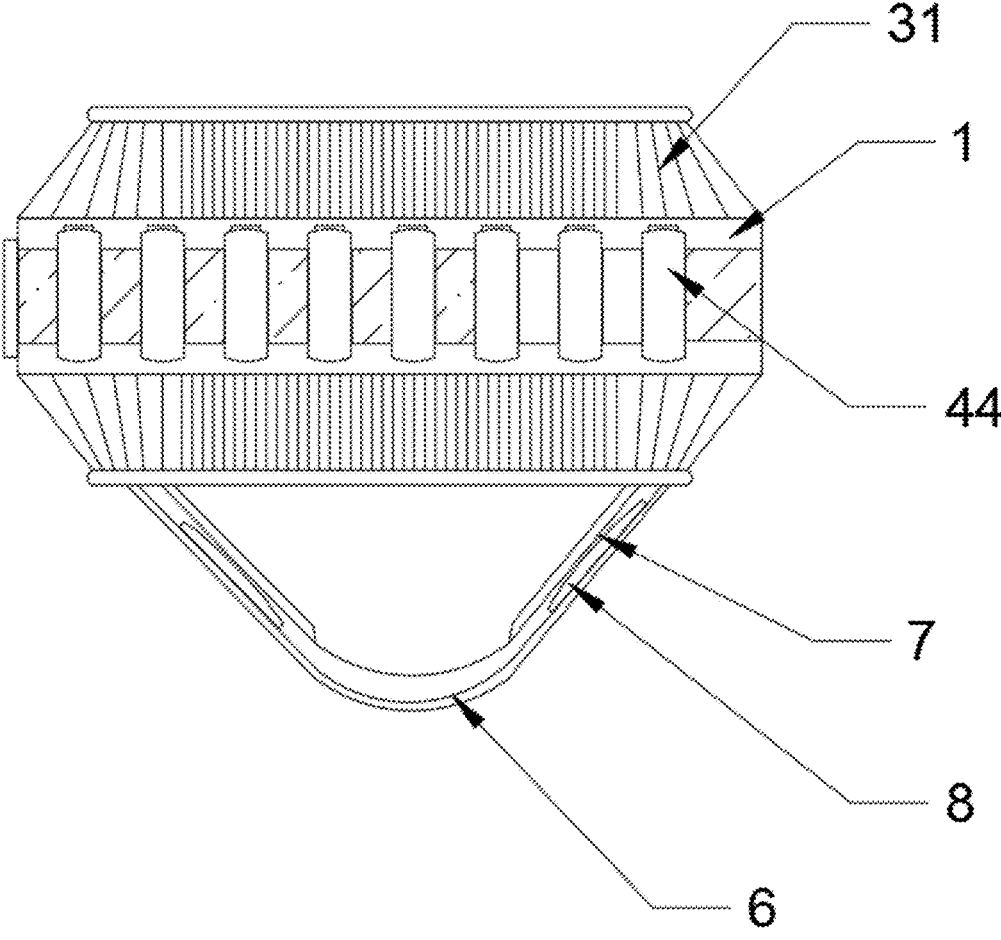
FIG. 5 illustrates a schematic structural diagram of a fixing strap, a limiting strap and a perineal pocket of the modular multifunctional pelvic fixation hemostatic device according to an embodiment of the disclosure.

In an embodiment, please refer to FIG. 1, FIG. 2 and FIG. 5, the auxiliary fixing assembly 3 includes: limiting straps 31, connection strips 32, racks 33, positioning brackets 34, limiting brackets 35, positioning racks 36, positioning rods 37, and first elastic elements 38. The limiting straps 31 are disposed on two sides of the fixing strap 1. Two ends of each limiting strap 31 proximate to the lock catch 2 are respectively provided with the connection strips 32, and a surface of each of the connection strips 32 is provided with the rack 33. Ends of the fixing strap 1 proximate to the lock catch 2 are fixedly provided with the positioning brackets 34, respectively. A side inside each positioning bracket 34 proximate to the rack 33 is fixedly provided with the limiting bracket 35, an inside of the limiting bracket 35 is provided with the positioning rack 36, and the positioning rack 36 is fixedly provided with the positioning rod 37 thereon. The positioning rod 37 penetrates through an end of the positioning bracket 34, an outside of the positioning rod 37 is sleeved with the first elastic element 38, and the first elastic element 38 is configured to adjust a position of the positioning rack 36 inside the limiting bracket 35, to make the positioning rack 36 be connected to the rack 33.

In the embodiment, the limiting strap 31 is made of a resilient material, and two ends of the limiting strap 31 are provided with the connection strips 32, a material of the connection strips 32 is plastic. The connection strip 32 is installed with the rack 33, a length of the rack 33 is the same as a length of the connection strip 32, the rack 33 penetrates through the positioning bracket 34, and the positioning rack 36 inside the positioning bracket 34 is meshed with the rack 33. The number of the limiting straps 31 is two, and the two limiting straps 31 are symmetrically disposed on the two sides of the fixing strap 1. Two ends of each limiting strap 31 are provided with the connection straps and positioning straps, which are convenient to form a cross to limit the position of the fixing strap 1, so as to stably install the fixing strap 1 on the pelvic position of the patient. A section shape of a tooth on the positioning rack 36 and a section shape of a tooth on the rack 33 are right-angled trapezoid. The first elastic element 38 can be a spring or rubber, and in the embodiment, the first elastic element 38 is the spring. The connection strip 32 can drive the rack 33 to rapidly penetrate through the positioning bracket 34; when the connection strip 32 moves in reverse, under an action of the first elastic element 38, the positioning rack 36 is meshed with the rack 33 to fix a position of the rack 33, thus further fixing the position of the limiting strap 31. When it is necessary to separate the positioning rack 36 from the rack 33, the positioning rod 37 is manually pulled to make the positioning rack 36 to compress the first elastic element 38, the positioning rack 36 is now separated from the rack 33, so as to facilitate remove the connection strip 32 from the positioning bracket 34, facilitate to operate, and quickly limit and fix the position of the fixing strap 1.

Embodiment 2

As shown in FIGS. 1-8, a modular multifunctional pelvic fixation hemostatic device is provided in the embodiment of the disclosure, and the hemostatic device includes a fixing strap 1, a lock catch 2, an auxiliary fixing assembly 3, a hemostatic assembly 4, press inflators 5, a perineal pocket 6, a hemostatic excipient pad 7, and an auxiliary compressing assembly 8.

The fixing strap 1 is configured to wrap around a pelvic position of a patient. Two ends of the lock catch 2 are respectively disposed on two ends of the fixing strap 1, and the lock catch 2 is configured to fix a length of the fixing strap 1 wrapped around the pelvic position of the patient. Two sides of the fixing strap 1 are provided with the auxiliary fixing assembly 3, and the auxiliary fixing assembly 3 is configured to fix the fixing strap 1 in the pelvic position of the patient.

The hemostatic assembly 4 is disposed on the fixing strap 1, and is configured to compress great vessels in a junctional area. The hemostatic assembly 4 is connected to the press inflators 5, and the press inflators 5 are configured to adjust a volume of the hemostatic assembly 4.

The perineal pocket 6 is disposed on a middle of the fixing strap 1, and is configured to cover and dress a perineum and buttocks of the patient. A surface of the perineal pocket 6 is provided with the hemostatic excipient pad 7, and an inside of the perineal pocket 6 is provided with the auxiliary compressing assembly 8, and the auxiliary compressing assembly 8 is configured to perform pressure hemostasis on a bone protrusion area and a depression area of the perineal and the buttocks of the patient.

In the embodiment, the pelvic position of the patient can be fixed through the fixing strap 1 and the lock catch 2, stability of the fixing strap 1 in the pelvic position of the patient is improved through the auxiliary fixing assembly 3, thus avoiding a movement of the fixing strap 1 during patient transporting, dragging, and other processes; the great vessels in the junctional area are effectively compressed through the hemostatic assembly 4 on the fixing strap 1, thus ensuring a compression hemostasis effect of the great vessels; the hemostatic excipient pad 7 is in full contact with wounds of the perineum and the buttocks of the patient through the auxiliary compressing assembly 8, thus covering and dressing the bone protrusion area and the depression area of the patient, an operation of the hemostatic device is convenient, so as to achieve integrated pelvic fixation, wound hemostasis, and dressing. The perineal pocket 6 is a triangular structure or a straight angle structure. When the perineal pocket 6 is the straight angle structure, a clip-style tourniquet is installed on an end of a part of the perineal pocket 6 proximate to a thigh of the patient, which can block active bleeding of lower limb wound caused by arterial blood supply from top to bottom, and has a certain hemostatic effect on inguinal wound bleeding caused by venous reflux from bottom to up.

In an embodiment, please refer to FIG. 1, FIG. 2 and FIG. 5, the auxiliary fixing assembly 3 includes: limiting straps 31, connection strips 32, racks 33, positioning brackets 34, limiting brackets 35, positioning racks 36, positioning rods 37, and first elastic elements 38. The limiting straps 31 are disposed on two sides of the fixing strap 1. Two ends of each limiting strap 31 proximate to the lock catch 2 are respectively provided with the connection strips 32, and a surface of each of the connection strips 32 is provided with the rack 33. Ends of the fixing strap 1 proximate to the lock catch 2 are fixedly provided with the positioning brackets 34, respectively. A side inside each positioning bracket 34 proximate to the rack 33 is fixedly provided with the limiting bracket 35, an inside of the limiting bracket 35 is provided with the positioning rack 36, and the positioning rack 36 is fixedly provided with the positioning rod 37 thereon. The positioning rod 37 penetrates through an end of the positioning bracket 34, an outside of the positioning rod 37 is sleeved with the first elastic element 38, and the first elastic element 38 is configured to adjust a position of the positioning rack 36 inside the limiting bracket 35, to make the positioning rack 36 be connected to the rack 33.

In the embodiment, the limiting strap 31 is made of a resilient material, and two ends of the limiting strap 31 are provided with the connection strips 32, a material of the connection strips 32 is plastic. The connection strip 32 is installed with the rack 33, a length of the rack 33 is the same as a length of the connection strip 32, the rack 33 penetrates through the positioning bracket 34, and the positioning rack 36 inside the positioning bracket 34 is meshed with the rack 33. The number of the limiting straps 31 is two, and the two limiting straps 31 are symmetrically disposed on the two sides of the fixing strap 1. Two ends of each limiting strap 31 are provided with the connection straps and positioning straps, which are convenient to form a cross to limit the position of the fixing strap 1, so as to stably install the fixing strap 1 on the pelvic position of the patient. A section shape of a tooth on the positioning rack 36 and a section shape of a tooth on the rack 33 are right-angled trapezoid. The first elastic element 38 can be a spring or rubber, and in the embodiment, the first elastic element 38 is the spring. The connection strip 32 can drive the rack 33 to rapidly penetrate through the positioning bracket 34; when the connection strip 32 moves in reverse, under an action of the first elastic element 38, the positioning rack 36 is meshed with the rack 33 to fix a position of the rack 33, thus further fixing the position of the limiting strap 31. When it is necessary to separate the positioning rack 36 from the rack 33, the positioning rod 37 is manually pulled to make the positioning rack 36 to compress the first elastic element 38, the positioning rack 36 is now separated from the rack 33, so as to facilitate remove the connection strip 32 from the positioning bracket 34, facilitate to operate, and quickly limit and fix the position of the fixing strap 1.

Figure 3:
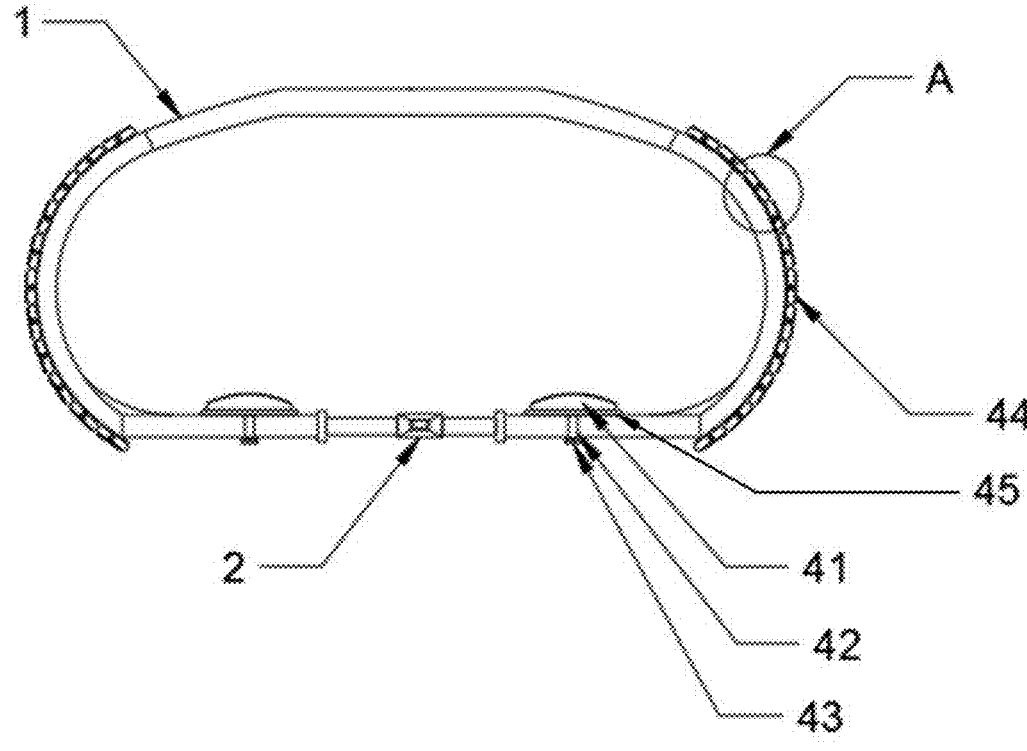
FIG. 3 illustrates a schematic structural diagram of a hemostatic assembly of the modular multifunctional pelvic fixation hemostatic device according to an embodiment of the disclosure.
Figure 4:
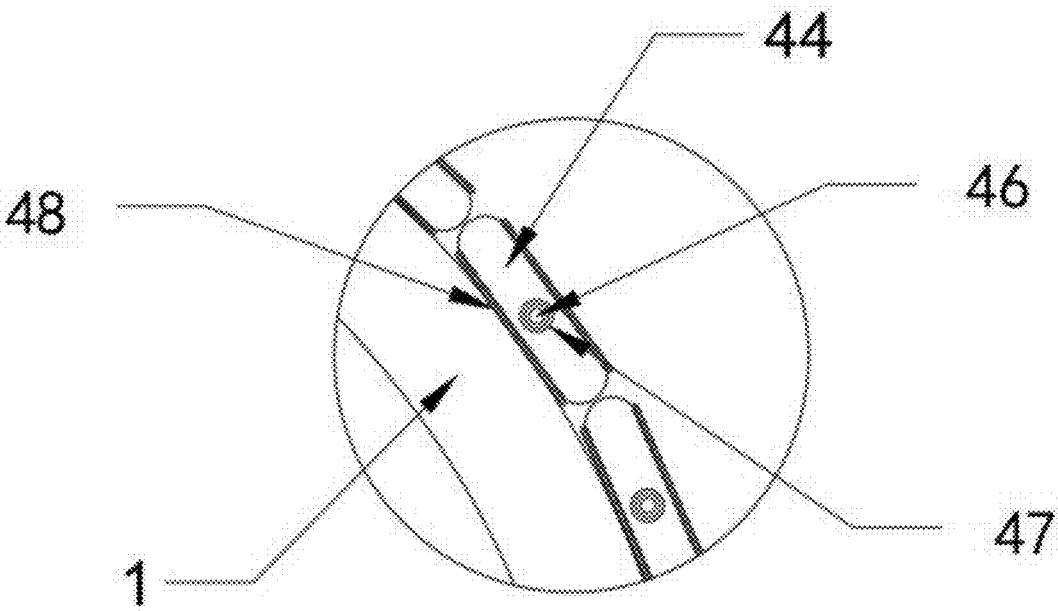
FIG. 4 illustrates a schematic structural diagram of an enlarged part A in FIG. 3 according to an embodiment of the disclosure.

In an embodiment, please refer to FIG. 1, FIG. 3 and FIG. 4, the hemostatic assembly 4 includes: first hemostatic air bags 41, first valves 43, second hemostatic air bags 44, first VELCRO-type fastening elements 45, second valves 47, and second VELCRO-type fastening elements 48.

The first hemostatic air bags 41 are disposed on ends of an inside of the fixing strap 1 proximate to the lock catch 2. A section shape of each first hemostatic air bag 41 is arc-shaped. Each first hemostatic air bag 41 is provided with the first VELCRO-type fastening element 45, and the first VELCRO-type fastening element 45 is configured to connect the first hemostatic air bag 41 and the fixing strap 1. Each first hemostatic air bag 41 defines a first air intake 42, and the first valve 43 is installed on the first air intake 42.

The second hemostatic air bags 44 are disposed on an outside of the fixing strap 1. A section shape of each second hemostatic air bags 44 is elliptical. A surface of each second hemostatic air bag 44 is provided with the second VELCRO-type fastening element 48, and the second VELCRO-type fastening element 48 is configured to connect the second hemostatic air bag 44 and the fixing strap 1. Each second hemostatic air bag 44 defines a second air intake 46, and the second valve 47 is installed on the second air intake 46.

In the embodiment, a shape of the first hemostatic air bag 41 is circular, the first hemostatic air bag 41 is connected to the fixing strap 1 through the first VELCRO-type fastening element 45, and a position of the first hemostatic air bag 41 on the fixing strap 1 can be adjusted through the first VELCRO-type fastening element 45, thus facilitating to contact with the great vessels in the junctional area. Air can enter the first hemostatic air bag 41 through the first valve 43 on the first air intake 42 using the press inflator 5, thereby to change the volume of the first hemostatic air bag 41, thus facilitating the first hemostatic air bag 41 to effectively compress the great vessels in the junctional area. The first hemostatic air bag 41 is further provided with a pressure detector, and the pressure detector can display a compression strength, so as to avoid undersized or excessive compression strength.

The number of the second hemostatic air bags 44 are multiple, and the multiple second hemostatic air bags 44 are evenly distributed on the outside of the fixing strap 1, and the second hemostatic air bag 44 is connected to the fixing strap 1 through the second VELCRO-type fastening element 48. The second hemostatic air bag 44 is in a long strip shape, and the second hemostatic air bag 44 defines the second air intake 46, and the second valve 47 is installed on the second air intake 46, thus facilitating the second hemostatic air bag 44 to be connected to the press inflator 5.

Embodiment 3

As shown in FIGS. 1-8, a modular multifunctional pelvic fixation hemostatic device is provided in the embodiment of the disclosure, and the hemostatic device includes a fixing strap 1, a lock catch 2, an auxiliary fixing assembly 3, a hemostatic assembly 4, press inflators 5, a perineal pocket 6, a hemostatic excipient pad 7, and an auxiliary compressing assembly 8.

The fixing strap 1 is configured to wrap around a pelvic position of a patient. Two ends of the lock catch 2 are respectively disposed on two ends of the fixing strap 1, and the lock catch 2 is configured to fix a length of the fixing strap 1 wrapped around the pelvic position of the patient. Two sides of the fixing strap 1 are provided with the auxiliary fixing assembly 3, and the auxiliary fixing assembly 3 is configured to fix the fixing strap 1 in the pelvic position of the patient.

The hemostatic assembly 4 is disposed on the fixing strap 1, and is configured to compress great vessels in a junctional area. The hemostatic assembly 4 is connected to the press inflators 5, and the press inflators 5 are configured to adjust a volume of the hemostatic assembly 4.

The perineal pocket 6 is disposed on a middle of the fixing strap 1, and is configured to cover and dress a perineum and buttocks of the patient. A surface of the perineal pocket 6 is provided with the hemostatic excipient pad 7, and an inside of the perineal pocket 6 is provided with the auxiliary compressing assembly 8, and the auxiliary compressing assembly 8 is configured to perform pressure hemostasis on a bone protrusion area and a depression area of the perineal and the buttocks of the patient.

In the embodiment, the pelvic position of the patient can be fixed through the fixing strap 1 and the lock catch 2, stability of the fixing strap 1 in the pelvic position of the patient is improved through the auxiliary fixing assembly 3, thus avoiding a movement of the fixing strap 1 during patient transporting, dragging, and other processes; the great vessels in the junctional area are effectively compressed through the hemostatic assembly 4 on the fixing strap 1, thus ensuring a compression hemostasis effect of the great vessels; the hemostatic excipient pad 7 is in full contact with wounds of the perineum and the buttocks of the patient through the auxiliary compressing assembly 8, thus covering and dressing the bone protrusion area and the depression area of the patient, an operation of the hemostatic device is convenient, so as to achieve integrated pelvic fixation, wound hemostasis, and dressing. The perineal pocket 6 is a triangular structure or a straight angle structure. When the perineal pocket 6 is the straight angle structure, a clip-style tourniquet is installed on an end of a part of the perineal pocket 6 proximate to a thigh of the patient, which can block active bleeding of lower limb wound caused by arterial blood supply from top to bottom, and has a certain hemostatic effect on inguinal wound bleeding caused by venous reflux from bottom to up.

In an embodiment, please refer to FIG. 1, FIG. 2 and FIG. 5, the auxiliary fixing assembly 3 includes: limiting straps 31, connection strips 32, racks 33, positioning brackets 34, limiting brackets 35, positioning racks 36, positioning rods 37, and first elastic elements 38. The limiting straps 31 are disposed on two sides of the fixing strap 1. Two ends of each limiting strap 31 proximate to the lock catch 2 are respectively provided with the connection strips 32, and a surface of each of the connection strips 32 is provided with the rack 33. Ends of the fixing strap 1 proximate to the lock catch 2 are fixedly provided with the positioning brackets 34, respectively. A side inside each positioning bracket 34 proximate to the rack 33 is fixedly provided with the limiting bracket 35, an inside of the limiting bracket 35 is provided with the positioning rack 36, and the positioning rack 36 is fixedly provided with the positioning rod 37 thereon. The positioning rod 37 penetrates through an end of the positioning bracket 34, an outside of the positioning rod 37 is sleeved with the first elastic element 38, and the first elastic element 38 is configured to adjust a position of the positioning rack 36 inside the limiting bracket 35, to make the positioning rack 36 be connected to the rack 33.

In the embodiment, the limiting strap 31 is made of a resilient material, and two ends of the limiting strap 31 are provided with the connection strips 32, a material of the connection strips 32 is plastic. The connection strip 32 is installed with the rack 33, a length of the rack 33 is the same as a length of the connection strip 32, the rack 33 penetrates through the positioning bracket 34, and the positioning rack 36 inside the positioning bracket 34 is meshed with the rack 33. The number of the limiting straps 31 is two, and the two limiting straps 31 are symmetrically disposed on the two sides of the fixing strap 1. Two ends of each limiting strap 31 are provided with the connection straps and positioning straps, which are convenient to form a cross to limit the position of the fixing strap 1, so as to stably install the fixing strap 1 on the pelvic position of the patient. A section shape of a tooth on the positioning rack 36 and a section shape of a tooth on the rack 33 are right-angled trapezoid. The first elastic element 38 can be a spring or rubber, and in the embodiment, the first elastic element 38 is the spring. The connection strip 32 can drive the rack 33 to rapidly penetrate through the positioning bracket 34; when the connection strip 32 moves in reverse, under an action of the first elastic element 38, the positioning rack 36 is meshed with the rack 33 to fix a position of the rack 33, thus further fixing the position of the limiting strap 31. When it is necessary to separate the positioning rack 36 from the rack 33, the positioning rod 37 is manually pulled to make the positioning rack 36 to compress the first elastic element 38, the positioning rack 36 is now separated from the rack 33, so as to facilitate remove the connection strip 32 from the positioning bracket 34, facilitate to operate, and quickly limit and fix the position of the fixing strap 1.

In an embodiment, please refer to FIG. 1, FIG. 3 and FIG. 4, the hemostatic assembly 4 includes: first hemostatic air bags 41, first valves 43, second hemostatic air bags 44, first VELCRO-type fastening elements 45, second valves 47, and second VELCRO-type fastening elements 48.

The first hemostatic air bags 41 are disposed on ends of an inside of the fixing strap 1 proximate to the lock catch 2. A section shape of each first hemostatic air bag 41 is arc-shaped. Each first hemostatic air bag 41 is provided with the first VELCRO-type fastening element 45, and the first VELCRO-type fastening element 45 is configured to connect the first hemostatic air bag 41 and the fixing strap 1.

Each first hemostatic air bag 41 defines a first air intake 42, and the first valve 43 is installed on the first air intake 42.

The second hemostatic air bags 44 are disposed on an outside of the fixing strap 1. A section shape of each second hemostatic air bags 44 is elliptical. A surface of each second hemostatic air bag 44 is provided with the second VELCRO-type fastening element 48, and the second VELCRO-type fastening element 48 is configured to connect the second hemostatic air bag 44 and the fixing strap 1. Each second hemostatic air bag 44 defines a second air intake 46, and the second valve 47 is installed on the second air intake 46.

In the embodiment, a shape of the first hemostatic air bag 41 is circular, the first hemostatic air bag 41 is connected to the fixing strap 1 through the first VELCRO-type fastening element 45, and a position of the first hemostatic air bag 41 on the fixing strap 1 can be adjusted through the first VELCRO-type fastening element 45, thus facilitating to contact with the great vessels in the junctional area. Air can enter the first hemostatic air bag 41 through the first valve 43 on the first air intake 42 using the press inflator 5, thereby to change the volume of the first hemostatic air bag 41, thus facilitating the first hemostatic air bag 41 to effectively compress the great vessels in the junctional area. The first hemostatic air bag 41 is further provided with a pressure detector, and the pressure detector can display a compression strength, so as to avoid undersized or excessive compression strength.

The number of the second hemostatic air bags 44 are multiple, and the multiple second hemostatic air bags 44 are evenly distributed on the outside of the fixing strap 1, and the second hemostatic air bag 44 is connected to the fixing strap 1 through the second VELCRO-type fastening element 48. The second hemostatic air bag 44 is in a long strip shape, and the second hemostatic air bag 44 defines the second air intake 46, and the second valve 47 is installed on the second air intake 46, thus facilitating the second hemostatic air bag 44 to be connected to the press inflator 5.

Figure 6:
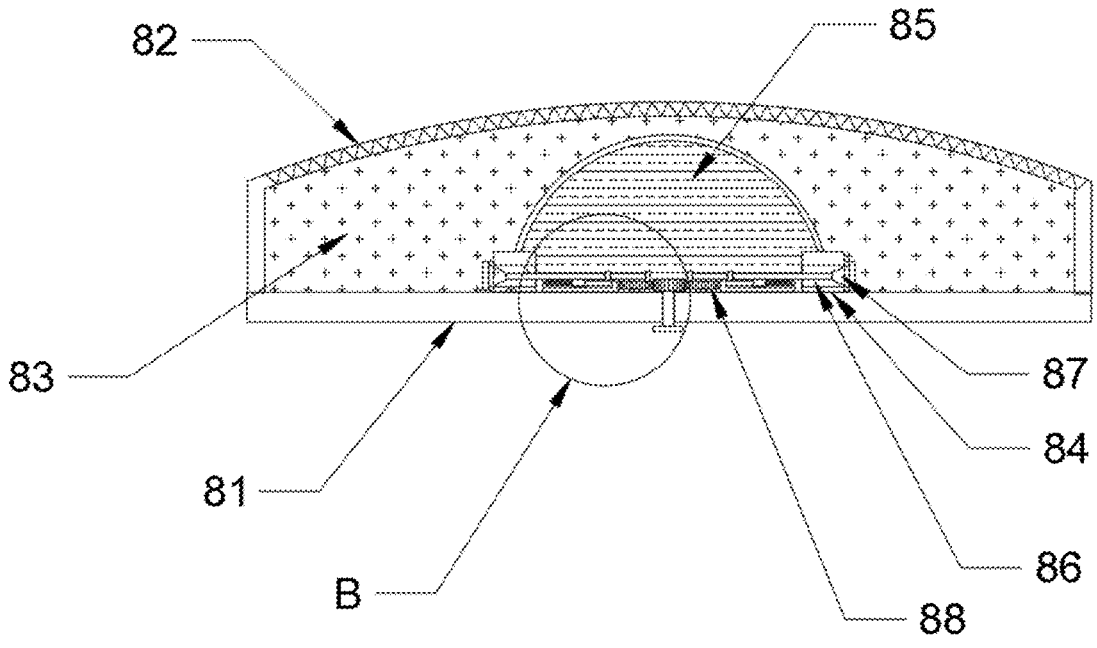
FIG. 6 illustrates a schematic structural diagram of an auxiliary compressing assembly of the modular multifunctional pelvic fixation hemostatic device according to an embodiment of the disclosure.

In an embodiment, please refer to FIG. 1, FIG. 5 and FIG. 6, the auxiliary compressing assembly 8 includes: a positioning plate 81, a resilient pad 82, a positioning ring 84, a water bag 85, scaling plugs 87, and an adjusting assembly 88.

The positioning plate 81 is disposed inside the perineal pocket 6. The positioning plate 81 is provided with the resilient pad 82 thereon, and the resilient pad 82 is filled with foaming agent powder therein. A middle of the positioning plate 81 is provided with the positioning ring 84 thereon, the positioning ring 84 is provided with the water bag 85 thereon, and the positioning ring 84 is in communication with an inside of the water bag 85.

The positioning ring 84 defines drain holes 86, and an inside of each of the drain holes 86 is provided with the sealing plug 87. An inside of the positioning ring 84 is provided with the adjusting assembly 88, and the adjusting assembly 88 is connected to the sealing plugs 87, and configured to adjust positions of the sealing plugs 87 on the drain holes 86, to thereby open and seal the drain holes 86.

In the embodiment, a shape of the resilient pad 82 is circular, and a section shape of the resilient pad 82 on the positioning plate 81 is arc-shaped. The inside of the resilient pad 82 is filled with the foaming agent powder 83, when the foaming agent powder 83 is mixed with water, it can be rapidly foamed and expanded, to adjust a volume of the resilient pad 82. When the foaming agent powder is foamed and expanded, the resilient pad 82 is driven to contact with the bone protrusion area and the depression area of the patient, thus facilitating to perform the pressure hemostasis and covering and dressing operations. The hemostatic excipient pad 7 on the surface of the perineal pocket 6 can be replaced and its position can be adjusted, thus facilitating to contact with the wound of the patient and perform a hemostatic operation. Through the foaming and expanding of the foaming agent powder 83, the hemostatic excipient pad 7 is in full contact with the wound of the patient, and the position of the hemostatic excipient pad 7 is fixed, so that the hemostatic excipient pad 7 is always in full contact with the wound of the patient. Water in the water bag 85 can be rapidly and evenly discharged through the drain holes 86 and the adjusting assembly 88, so that the water is in full contact with the foaming agent powder 83, and the foaming agent powder is foamed and expanded to adjust the volume of the resilient pad 82. The perincal pocket 6 is disposed as two layers, the auxiliary compressing assembly 8 is disposed between the two layers of the perineal pocket 6, a whole shape of the auxiliary compressing assembly 8 is circular, and the auxiliary compressing assembly 8 can be taken out from the inside of the perineal pocket 6, and a position of the auxiliary compressing assembly 8 inside the perineal pocket 6 can be adjusted, thereby to cover a position corresponding to the wound of the patient.

The second hemostatic air bags 44 can be also installed inside the perineal pocket 6, and full contact between the hemostatic excipient pad 7 and the wound of the patient can be achieved through assembling multiple second hemostatic air bags 44.

Figure 7:
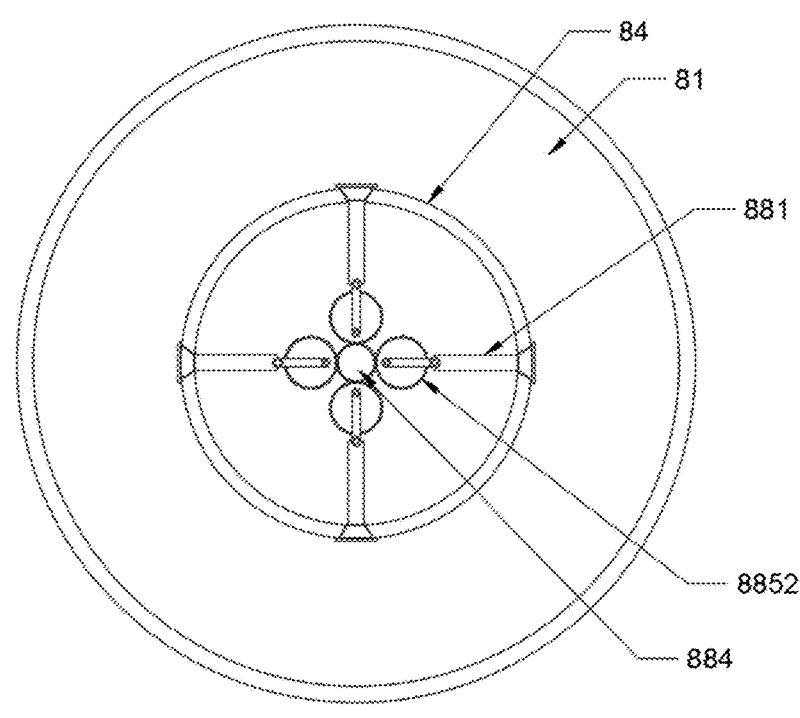
FIG. 7 illustrates a schematic structural diagram of a positioning plate and an inside of a positioning ring of the modular multifunctional pelvic fixation hemostatic device according to an embodiment of the disclosure.
Figure 8:
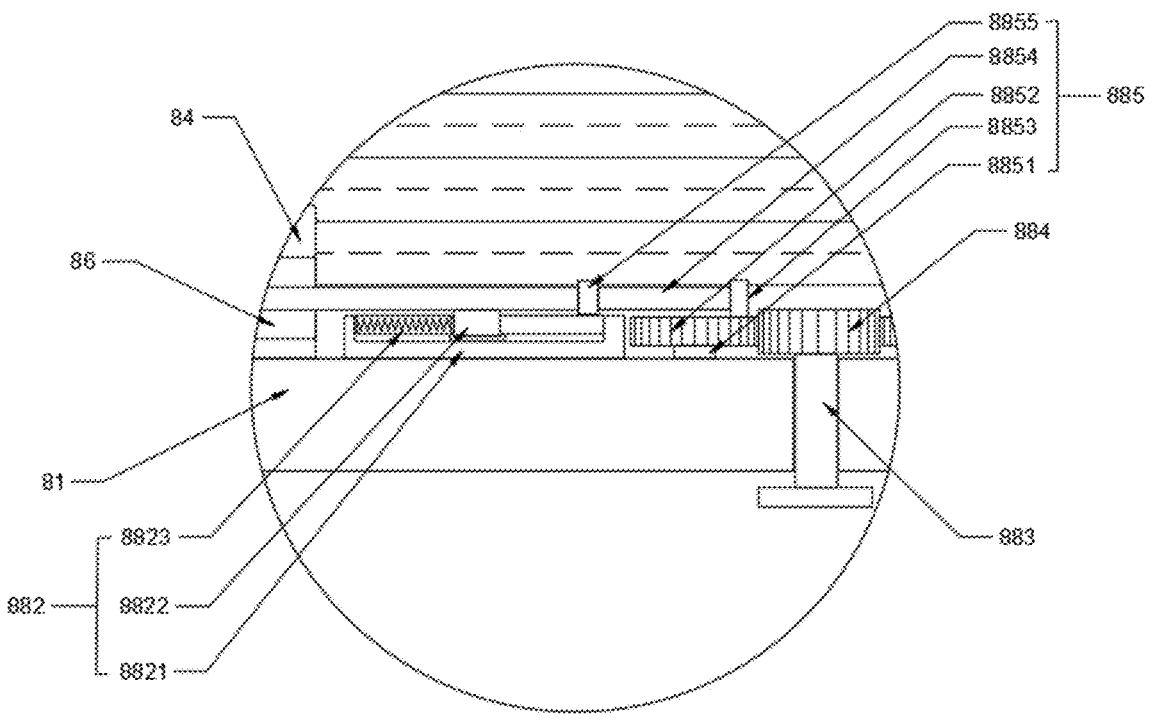
FIG. 8 illustrates a schematic structural diagram of an enlarged part B in FIG. 6 according to an embodiment of the disclosure.

In an embodiment, please refer to FIGS. 6-8, the adjusting assembly includes: moving rods 881, limiting assemblies 882, a drive rod 883, a drive rack 884, and connection assembles 885.

Each moving rod 881 is fixedly connected to the sealing plug 87, and is disposed inside the positioning ring 84. Each limiting assembly 882 is disposed between the corresponding moving rod 881 and the positioning plate 81, and each limiting assembly 882 is configured to limit a moving track of the moving rod 881, and adjust a position of the moving rod 881.

The drive rod 883 is disposed on a middle of the positioning plate 81, and is fixedly connected to the middle of the positioning plate 81. An end of the drive rod 883 inside the positioning ring 84 is fixedly provided with the drive rack 884, each connection assembly 885 is disposed between the drive rack 884 and the corresponding moving rod 881, and each connection assembly 885 is configured to move a position of the moving rod 881 when the drive rod 883 and the drive rack 884 rotate, to thereby make the sealing plug 87 away from the drain hole 86.

In the embodiment, the end of the moving rod 881 is connected to the sealing plug 87, and another end of the moving rod 881 is connected to the connection assembly 885. A shape of the sealing plug 87 is a frustum of a cone, which is convenient to seal the drain hole 86. The drain holes 86, the sealing plugs 87, the limiting assembles 882 and the connection assemblies 885 are all provided with multiple sets, and are evenly distributed on the positioning ring 84 and the positioning plate 81. When the drive rod 883 is manually rotated, the drive rack 884 is driven to rotate, multiple sealing plugs 87 are kept away from the drain holes 86 at the same time through the connection assemblies 885, which is convenient for the water in the water bag 85 to uniformly contact with the foaming agent powder 83.

In an embodiment, please refer to FIGS. 6-8, each limiting assembly 882 includes: a slide rail 8821, a moving block 8822, and a second elastic element 8823.

The slide rail 8821 is fixedly disposed on the positioning plate 81, and is located inside the positioning ring 84. An inside of the slide rail 8821 is provided with the moving block 8822, and the moving block 8822 is fixedly connected to an outer wall of the moving rod 881. The moving block 8822 is slidably connected to the slide rail 8821, and the slide rail 8821 is configured to keep the moving rod 881 moving along an inside of the slide rail 8821; specifically, the slide rail 8821 may include two protrusions, a groove is defined between the two protrusions, and the moving rod 881 is disposed in the groove, and the two protrusions are configured to keep the moving rod 881 moving along an inside of the slide rail 8821. The second elastic element 8823 is disposed between the moving block 8822 and the inside of the slide rail 8821.

In the embodiment, the second elastic element 8823 can be a spring or rubber, and in the embodiment, the second elastic element 8823 is the spring. An end of the second elastic element 8823 is connected to the moving block 8822, and another end of the second elastic element 8823 is connected to an end inside the slide rail 8821. The second elastic element 8823 is disposed on an end inside the slide rail 8821 proximate to the drain hole 86, and the second elastic element 8823 can adjust a position of the moving block 8822 inside the slide rail 8821, which is convenient to adjust the position of the moving rod 881. Under an action of the second elastic element 8823, the sealing plug 87 on the end of the moving rod 881 is tightly connected to the drain hole 86, which is convenient for the sealing plug 87 to seal the drain hole 86, in this case, the water in the water bag 85 cannot be in contact with the foaming agent powder 83 outside the positioning ring 84.

A section shape of the moving block 8822 is inverted T-shaped, the moving block 8822 is connected to the inside of the slide rail 8821, and the moving block 8822 can be slid along the inside of the slide rail 8821, to further limit the moving track of the moving rod 881, so that the moving rod 881 always moves along a straight direction during moving, which is convenient for the sealing plug 87 to be connected to or separated from the drain hole 86 on the positioning ring 84.

In an embodiment, please refer to FIGS. 6-8, each connection assembly 885 includes: a fixing rod 8851, a connection rack 8852, a first rotating bracket 8853, a connection rod 8854, and a second rotating bracket 8855.

The fixing rod 8851 is disposed on the positioning plate 81, and is located on a side of the drive rod 883. An outside of the fixing rod 8851 is provided with the connection rack 8852, and the connection rack 8852 is rotatably connected to the fixing rod 8851. A surface of the connection rack 8852 is provided with the first rotating bracket 8853, and an outside of the first rotating bracket 8853 is provided with the connection rod 8854. An end of the connection rod 8854 facing away from the first rotating bracket 8853 is provided with the second rotating bracket 8855, and the second rotating bracket 8855 is fixedly connected to the moving rod 881.

In the embodiment, the fixing rod 8851 is fixedly disposed on the positioning plate 81, and is located on the side of the drive rod 883. A rolling bearing is disposed between the fixing rod 8851 and the connection rack 8852, the connection rack 8852 can be stably rotated on the fixing rod 8851, and the connection rack 8852 is meshed with the drive rack 884. A side of the connection rack 8852 facing away from the fixing rod 8851 is fixedly provided with the first rotating bracket 8853, the first rotating bracket 8853 is located on the connection rack 8852 facing away from a center of the connection rack 8852, and a rolling bearing is disposed between the first rotating bracket 8853 and the connection rod 8854. The second rotating bracket 8853 is fixedly disposed on the end of the moving rod 881 facing away from the sealing plug 87, and a rolling bearing is disposed between the second rotating bracket 8855 and the connection rod 8854. When the connection rack 8852 is rotated, a position of the first rotating bracket 8853 is adjusted, to further achieve a position movement of the moving rod 881 along the slide rail 8821, so as to achieve a separation of the sealing plug 87 and the drain hole 86 driven by the moving rod 881, and achieve the water in the water bag 85 to be discharged through the drain hole 86 and in contact with the foaming agent powder 83. An end of the drive rod 883 extending out the positioning plate 81 is fixedly provided with a handle, and the handle is used to manually rotate the drive rod 883, to further rotate the drive rack 884. The number of the connection assemblies 885 is multiple, and the multiple connection racks 8852 are meshed with the drive rack 884. When the drive rack 884 is rotated, the multiple connection racks 8852 are driven to rotate at the same time, the multiple sealing plugs 87 are driven to separate from the drain holes 86 at the same time, the water in the water bag 85 is driven to in even contact with the foaming agent powder 83, so as to make the foaming agent powder be rapidly and evenly foamed and expanded. A working principle of the disclosure is as follows.

In the disclosure, the fixing strap 1 is wrapped around the pelvic position of the patient, and is fixed through the lock catch 2. The connection strip 32 is manually passed through the positioning bracket 34, under the action of the first elastic element 38, the positioning rack 36 can fix a position of the rack 33 on the connection strip 32, thus further achieving a position fixation of the fixing strap 1 by the limiting strap 31. An output end of the press inflator 5 is connected to the first air intake 42 of the first hemostatic air bag 41, and the first valve 43 is opened to make air enter the first hemostatic air bag 41, thus increasing the volume of the first hemostatic air bag 41 to fully compress the great vessels in the junctional area, and observing a value on the pressure detector in real-time. The second hemostatic air bag 44 is inserted between the fixing strap 1 and the wound of the patient, and the second hemostatic air bag 44 is expanded through the press inflator 5, to make the hemostatic excipient pad 7 in full contact with the wound of the patient. When there is a wound in the perineum or the buttocks of the patient, the drive rod 883 can be manually rotated to rotate the connection rack 8852 on the fixing rod 8851, the positions of the moving rod 881 and the sealing plug 87 are adjusted through the first rotating bracket 8853, the connection rod 8854 and the second rotating bracket 8855, the water in the water bag 85 is in full contact with the foaming agent powder 83 inside the resilient pad 82, and the foaming agent powder 83 is foamed and expanded to change the volume of the resilient pad 82, the hemostatic excipient pad 7 is in contact with the bone protrusion area and the depression area of the patient, which is convenient to covering and dressing, and is easy to use.

The above is merely embodiments of the disclosure and is not intended to limit it. Any modifications, equivalent substitutions, and improvements made within a spirit and principle of the disclosure shall be included within a scope of protection of the disclosure.

In addition, it should be understood that although this specification is described according to implementation methods, not each implementation method merely includes an independent technical solution. This description in the specification is for clarity only. Those skilled in the art should treat the specification as a whole, and the technical solutions in each embodiment can be appropriately combined to form other implementation methods that those skilled in the art can understand.

What is claimed is:

1. A modular multifunctional pelvic fixation hemostatic device, comprising:

a fixing strap, configured to wrap around a pelvic position of a patient;

a lock catch, wherein two ends of the lock catch are respectively disposed on two ends of the fixing strap, and the lock catch is configured to fix a length of the fixing strap wrapped around an outside of the pelvic position of the patient;

an auxiliary fixing assembly, disposed on two sides of the fixing strap, wherein the auxiliary fixing assembly is configured to fix the fixing strap on the pelvic position of the patient;

a hemostatic assembly, disposed on the fixing strap, and configured to compress great vessels in a junctional area;

press inflators, connected to the hemostatic assembly; wherein the press inflators are configured to adjust a volume of the hemostatic assembly; and a perineal pocket, disposed on a middle of the fixing strap, and configured to cover and dress a perineum and buttocks of the patient;

a hemostatic excipient pad, disposed on a surface of the perineal pocket; and an auxiliary compressing assembly, disposed on an inside of the perineal pocket; wherein the auxiliary compressing assembly is configured to perform pressure hemostasis on a bone protrusion area and a depression area of the perineum and the buttocks of the patient; and the auxiliary compressing assembly comprises:

a positioning plate, disposed inside the perineal pocket;

a resilient pad, disposed on the positioning plate; wherein the resilient pad is filled with foaming agent powder therein;

a positioning ring, disposed on a middle of the positioning plate;

a water bag, disposed on the positioning ring; wherein the positioning ring is in communication with an inside of the water bag; and the positioning ring defines drain holes;

sealing plugs, disposed in the drain holes, respectively; and an adjusting assembly, disposed inside the positioning ring and connected to the sealing plugs; wherein the adjusting assembly is configured to adjust positions of the sealing plugs on the drain holes, to thereby open and seal the drain holes.

2. The modular multifunctional pelvic fixation hemostatic device as claimed in claim 1, wherein the auxiliary fixing assembly comprises:

limiting straps, disposed on the two sides of the fixing strap, respectively;

connection strips, disposed on two ends of each of the limiting straps proximate to the lock catch, respectively;

racks, disposed on surfaces of the connection strips, respectively;

positioning brackets, fixedly installed on ends of the fixing strap proximate to the lock catch, respectively;

limiting brackets, disposed in the positioning brackets and disposed proximate to the racks, respectively;

positioning racks, disposed in the limiting brackets, respectively;

positioning rods, fixedly installed on the positioning racks, respectively; wherein each of the positioning rods penetrate through an end of the positioning bracket; and first elastic elements, sleeved on outsides of the positioning rods, respectively; wherein each of the first elastic elements is configured to adjust a position of the positioning rack inside the limiting bracket, to make the positioning rack be connected to the rack.

3. The modular multifunctional pelvic fixation hemostatic device as claimed in claim 1, wherein the hemostatic assembly comprises:

first hemostatic air bags, disposed on ends of an inside of the fixing strap proximate to the lock catch, respectively; wherein a section shape of each of the first hemostatic air bags is arc-shaped, and each of the first hemostatic air bags defines a first air intake;

first valves, installed on the first air intakes of the first hemostatic air bags, respectively;

first fastening elements, installed on the first hemostatic air bags, respectively;

wherein each of the first fastening elements is configured to connect the first hemostatic air bag and the fixing strap;

second hemostatic air bags, disposed on an outside of the fixing strap; wherein a section shape of each of the second hemostatic air bags is elliptical; and each of the second hemostatic air bags defines a second air intake;

second valves, installed on the second air intakes of the second hemostatic air bags, respectively; and second fastening elements, installed on surfaces of the second hemostatic air bags, respectively; wherein each of the second fastening elements is configured to connect the second hemostatic air bag and the fixing strap.

4. The modular multifunctional pelvic fixation hemostatic device as claimed in claim 1, wherein the adjusting assembly comprises:

moving rods, fixedly connected to the sealing plugs, respectively; wherein the moving rods are disposed inside the positioning ring;

limiting assembles, wherein each of the limiting assembles is disposed between a corresponding one of the moving rods and the positioning plate, and each of the limiting assemblies is configured to limit a moving track of the moving rod, and adjust a position of the moving rod; and a drive rod, disposed on the middle of the positioning plate; wherein the drive rod is fixedly connected to the middle of the positioning plate;

a drive rack, fixedly installed on an end of the drive rod located inside the positioning ring;

connection assemblies, wherein each of the connection assemblies is disposed between the drive rack and a corresponding one of the moving rods, and each of the connection assemblies is configured to move the position of the moving rod when the drive rod and the drive rack rotate, to thereby make the sealing plug away from the drain hole.

5. The modular multifunctional pelvic fixation hemostatic device as claimed in claim 4, wherein each of the limiting assembles comprises:

a slide rail, fixedly disposed on the positioning plate, and located inside the positioning ring;

a moving block, disposed inside the slide rail and fixedly connected to an outer wall of the moving rod; wherein the moving block is slidably connected to the slide rail, and the slide rail is configured to keep the moving rod moving inside the slide rail; and a second elastic element, disposed between the moving block and the slide rail.

6. The modular multifunctional pelvic fixation hemostatic device as claimed in claim 5, wherein each of the connection assemblies comprises:

a fixing rod, disposed on the positioning plate, and located on a side of the drive rod;

a connection rack, installed on an outside of the fixing rod and rotatably connected to the fixing rod;

a first rotating bracket, disposed on a surface of the connection rack;

a connection rod, disposed on an outside of the first rotating bracket;

a second rotating bracket, disposed on an end of the connection rod facing away from the first rotating bracket; wherein the second rotating bracket is fixedly connected to the corresponding moving rod; and the drive rack is meshed with the connection rack.

7. The modular multifunctional pelvic fixation hemostatic device as claimed in claim 5, wherein the second elastic element is disposed on an end inside the slide rail proximate to the drain hole.

* * * * *